US00PP14297P29

(12) United States Plant Patent
Koeze

(10) Patent No.: US PP14,297 P2
(45) Date of Patent: Nov. 11, 2003

(54) BEGONIA PLANT NAMED 'BBSIRIUS'

(50) Latin Name: *Begonia elatior (Begonia)*
Varietal Denomination: Bbsirius

(76) Inventor: Bert Koeze, Vledderveld 5, 2151 JS Nieuw Vennep (NL)

( * ) Notice: Subject to any disclaimer, the term of this patent is extended or adjusted under 35 U.S.C. 154(b) by 0 days.

(21) Appl. No.: 10/157,365

(22) Filed: May 28, 2002

(51) Int. Cl.[7] ..... A01H 5/00
(52) U.S. Cl. ..... Plt./348
(58) Field of Search ..... Plt./348, 349

*Primary Examiner*—Bruce R. Campell
*Assistant Examiner*—Susan B. McCormick
(74) *Attorney, Agent, or Firm*—Webb Ziesenheim Logsdon Orkin & Hanson P.C.

(57) ABSTRACT

A new and distinct begonia plant with red colored flowers.

1 Drawing Sheet

Varietal denomination: 'Bbsirius'.
Botanical classification: *Begonia elatior* (Begonia).

BACKGROUND OF THE INVENTION

The present invention comprises a new and distinct cultivar of *Begonia elatior* known by the varietal name 'Bbsirius'. The new variety was discovered in Aalsmeer, The Netherlands, in 1998. The new variety is a product of a planned breeding program and is a cross of an unnamed, unpatented variety of *Begonia tuberosa* (female) and an unnamed, unpatented variety of *Begonia socotrana* (male). The breeding program is directed to establishing various phenotype characteristics. The new variety differs in its flower color and its double flowers as compared to its parents. The new variety was first asexually reproduced by cuttings in Aalsmeer, The Netherlands. The new variety has been trial and field tested and has been found to retain its distinctive characteristics and remain true to type through successive propagations.

The new variety, when grown in a glass greenhouse has a response time for rooting from a terminal cutting of 14–18 days.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions by cuttings in a controlled greenhouse environment. Plants for the description were two (2) years old. Color references are primarily to The R.H.S. Colour Chart of The Royal Horticultural Society of London.

PLANT

Form: Upright.
Growth: Moderate.
Time to initiate roots: About 14–18 days.
Time to develop roots: 30 days.
Rooting habit: Fine, fibrous, well-branched.

Height: 30 cm from the media surface to the top of the leaf plane.
Width: 40 cm.
Internode length: 1.0–1.5 cm.
Lateral branches:
- *Number.*—4–5.
- *Length.*—1.0–1.5 cm.

Leaves:
- *Arrangement.*—Alternate.
- *Shape.*—Rounded.
- *Size.*—4–6 cm long; 5–6 cm wide.
- *Quantity.*—5–6 per lateral branch.
- *Petiole.*—4–5 cm long; 5 mm diameter; 143B.
- *Stipules.*—1 cm.
- *Margin.*—Irregular; serrated.
- *Texture.*—Smooth; shiny and leathery.
- *Color.*—Upper Surface: 131A. Lower Surface: 135B.
- *Venation.*—Pattern: Palmate. Color: 138B.

FLOWERS

Habit: Continuous flowering.
Shape: Rounded.
Aspect: Flat to cupped.
Size: 5–6 cm in diameter; 1–1.5 cm deep.
Fragrance: None.
Flower buds:
- *Length.*—2.5 cm.
- *Width.*—2.0 cm.
- *Size.*—2–3 cm long; 2.5 cm wide.
- *Color.*—50B.
- *Rate of flower opening.*—3 days.

Petals:
- *Arrangement.*—Double.
- *Shape.*—Oval.
- *Margin.*—Entire with irregularities.
- *Quantity.*—15–20 per flower.
- *Size.*—2.5 cm long; 4 cm wide.
- *Texture.*—Smooth.
- *Color.*—57B, both surfaces.

Peduncles:
- *Angle.*—Mostly erect.
- *Strength.*—Strong.
- *Length.*—3.0–3.5 cm.
- *Color.*—47A.

Pedicels:

*Angle.*—About 30 to 45° from vertical.
*Strength.*—Strong.
*Length.*—3.0–3.5 cm.
*Color.*—50B.

REPRODUCTIVE ORGANS

Stamens: None observed.
Pistils: None observed.

Disease resistance: Mildew tolerant.

Seed production: Seed production has not been observed as reproductive organs are not formed.

I claim:

1. A new and distinct variety of begonia plant substantially as shown and described.

* * * * *

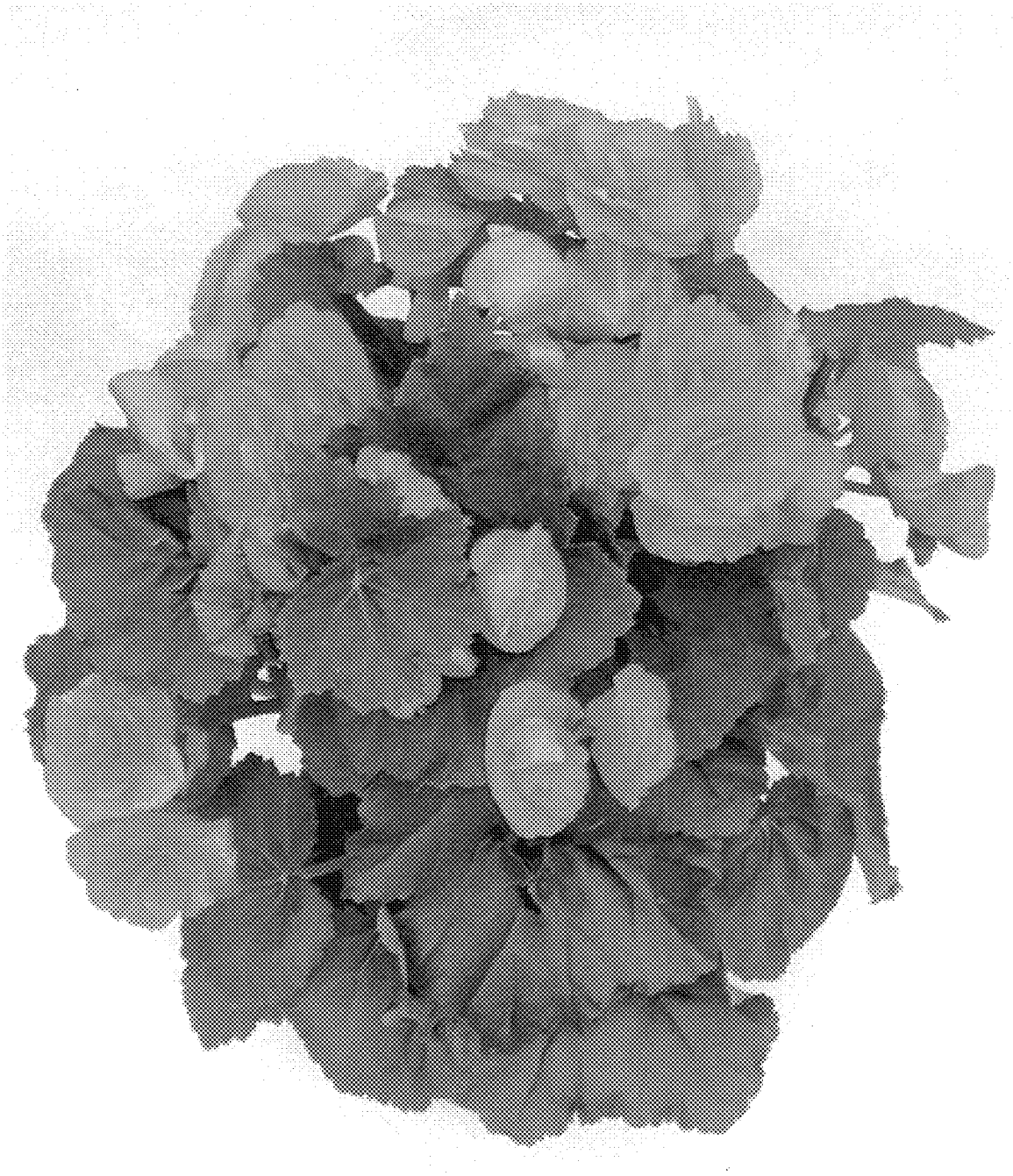

UNITED STATES PATENT AND TRADEMARK OFFICE

CERTIFICATE OF CORRECTION

PATENT NO. : PP14,297 P2
DATED : November 11, 2003
INVENTOR(S) : Bert Koeze

It is certified that error appears in the above-identified patent and that said Letters Patent is hereby corrected as shown below:

Title page,
Item [73], Assignee, insert -- Begonia Breeders Association B.V., Ev Aalsmere (NL) --
Item [30], Foreign Application Priority Data, insert:
-- May 28, 2001 (EP)……. 2001-0854 --.

Signed and Sealed this

Twenty-seventh Day of April, 2004

JON W. DUDAS
*Acting Director of the United States Patent and Trademark Office*